United States Patent [19]

Williams et al.

[11] Patent Number: 5,728,077
[45] Date of Patent: Mar. 17, 1998

[54] INTRAVENOUS DELIVERY SYSTEM

[75] Inventors: Robert Paul Williams; Rodney John Taylor, both of New South Wales, Australia

[73] Assignee: Health Care Technology Australia PTY. Ltd., Seven Hills, New South Wales, Australia

[21] Appl. No.: 416,749

[22] PCT Filed: Oct. 8, 1993

[86] PCT No.: PCT/AU93/00515

§ 371 Date: Mar. 26, 1996

§ 102(e) Date: Mar. 26, 1996

[87] PCT Pub. No.: WO94/08646

PCT Pub. Date: Apr. 28, 1994

[30] Foreign Application Priority Data

Oct. 15, 1992 [AU] Australia .................. PL5294

[51] Int. Cl.⁶ .................................. A61M 5/00
[52] U.S. Cl. ........................... 604/246; 604/260
[58] Field of Search .................... 604/246, 247, 604/248, 254, 259, 260, 80, 30

[56] References Cited

U.S. PATENT DOCUMENTS

| | | |
|---|---|---|
| 2,578,374 | 12/1951 | Pratt . |
| 2,771,878 | 11/1956 | Folland et al. . |
| 3,647,117 | 3/1972 | Hargest . |
| 3,895,631 | 7/1975 | Buckles et al. . |
| 3,895,741 | 7/1975 | Nugent . |
| 3,949,744 | 4/1976 | Clarke . |
| 4,137,915 | 2/1979 | Kamen . |
| 4,137,940 | 2/1979 | Faisandier . |
| 4,455,139 | 6/1984 | Gordon et al. . |
| 4,722,732 | 2/1988 | Martin . |
| 5,135,497 | 8/1992 | Hessel et al. . |
| 5,163,909 | 11/1992 | Stewart . |

FOREIGN PATENT DOCUMENTS

| | | |
|---|---|---|
| 565450 | 9/1987 | Australia . |
| 0 034 671 | 2/1980 | European Pat. Off. . |
| 0 041 182 | 5/1981 | European Pat. Off. . |
| 2 608 928 | 2/1988 | France . |
| 25 08 735 | 2/1975 | Germany . |
| 25 55 291 | 6/1977 | Germany . |
| WO91/09636 | 7/1991 | WIPO . |

*Primary Examiner*—Michael Powell Buiz
*Assistant Examiner*—N. Kent Gring
*Attorney, Agent, or Firm*—Larson & Taylor

[57] ABSTRACT

An intravenous delivery system for delivering a volume of solution to a patient intravenously from a solution container positioned above the patient and coupled to the patient via a length of narrow flexible tube. The system comprises frame means to support the solution container above the solution delivery outlet, means to raise the container as it empties to ensure a constant head of pressure, pointer displaceable about a calibrated scale on the frame means, the pointer being adapted to move with the container to provide visual indication of the volume of solution deliver to the patient, cut-off means to prevent flow of solution through the tube and means to trigger the cut-off means in response to a preselected position of the pointer.

17 Claims, 8 Drawing Sheets

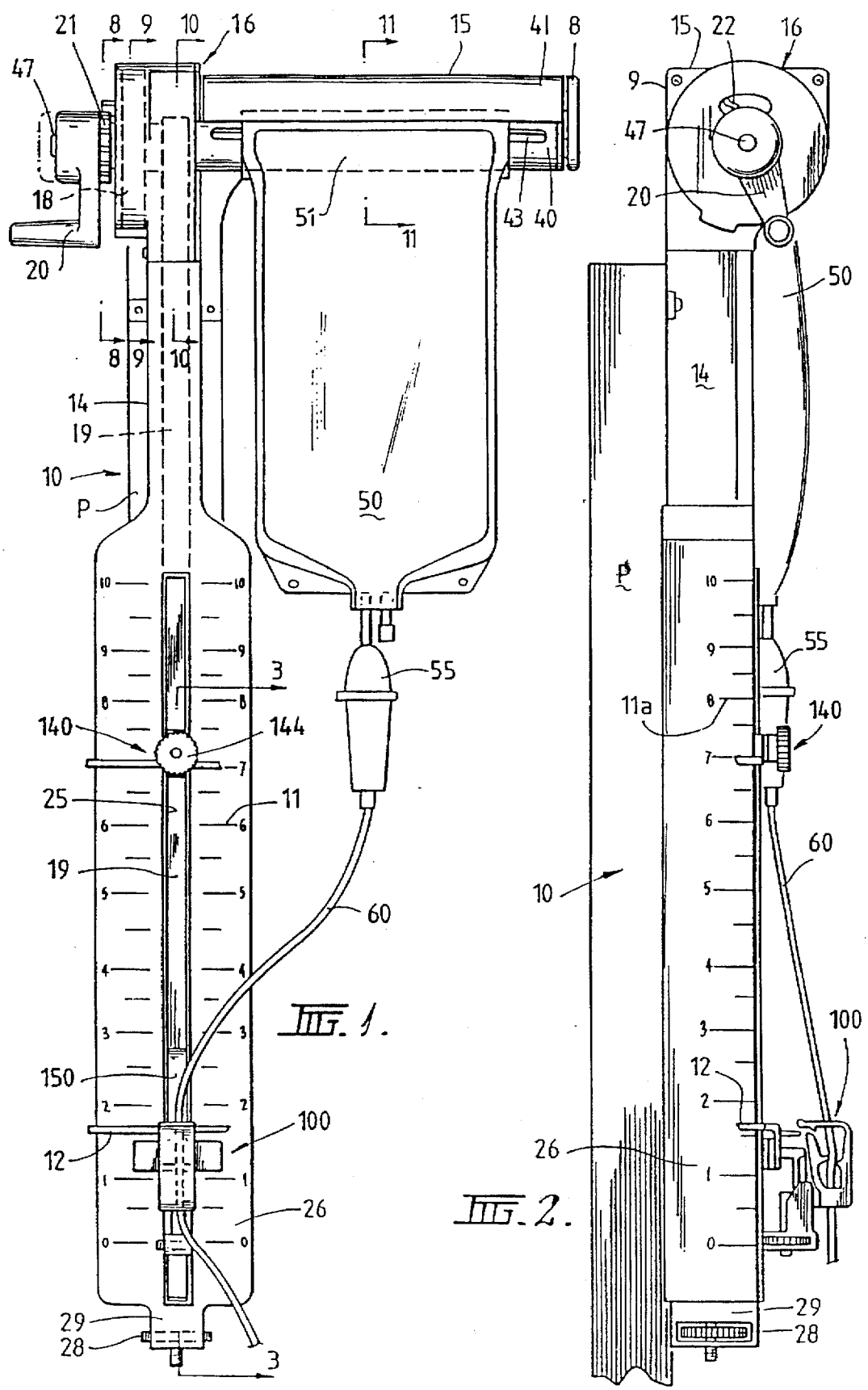

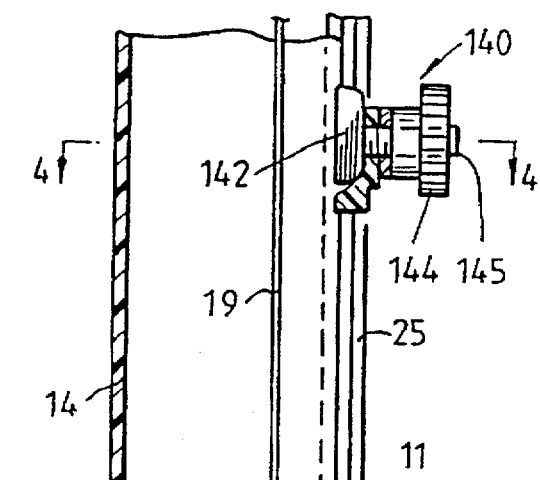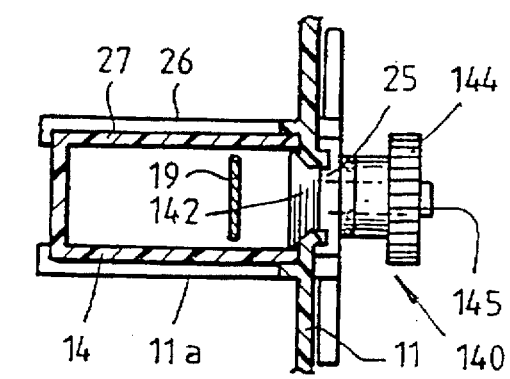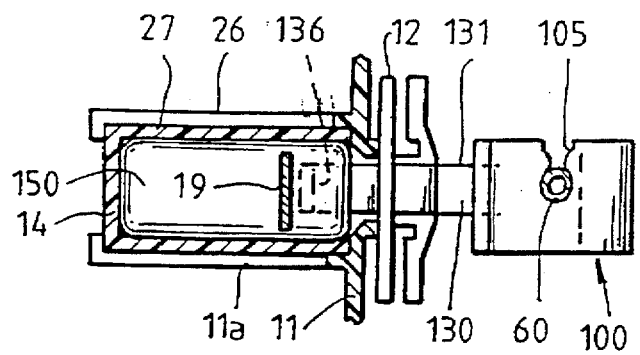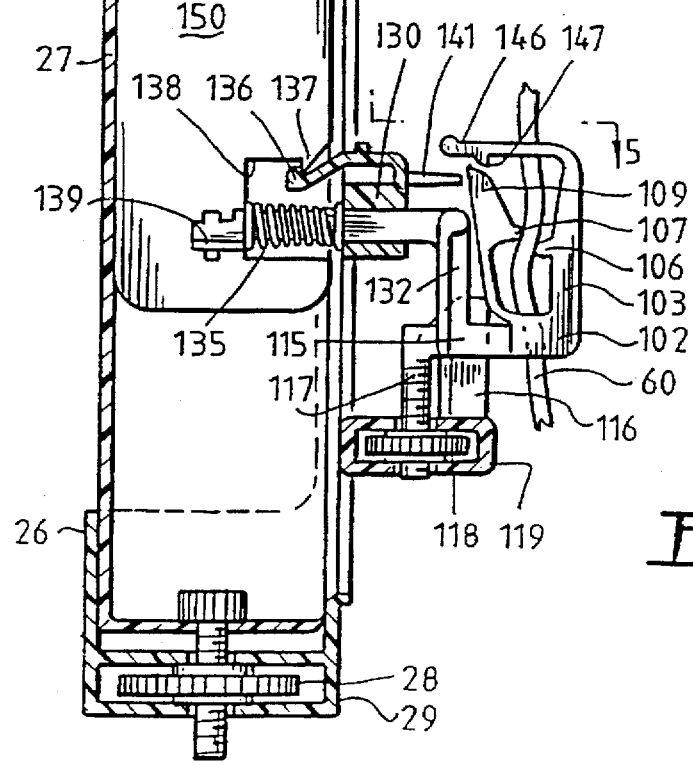
FIG. 4.
FIG. 5.
FIG. 3.

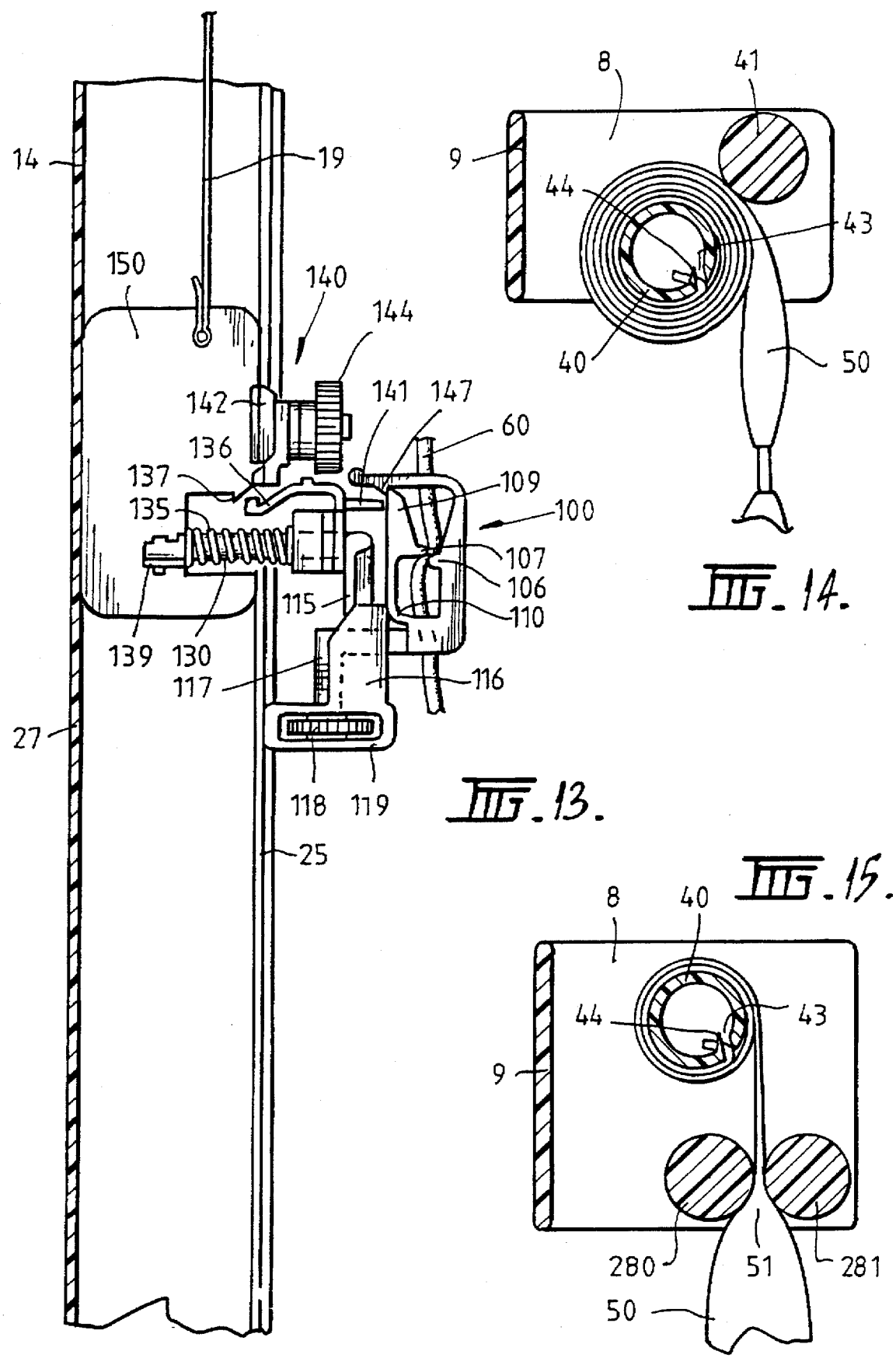

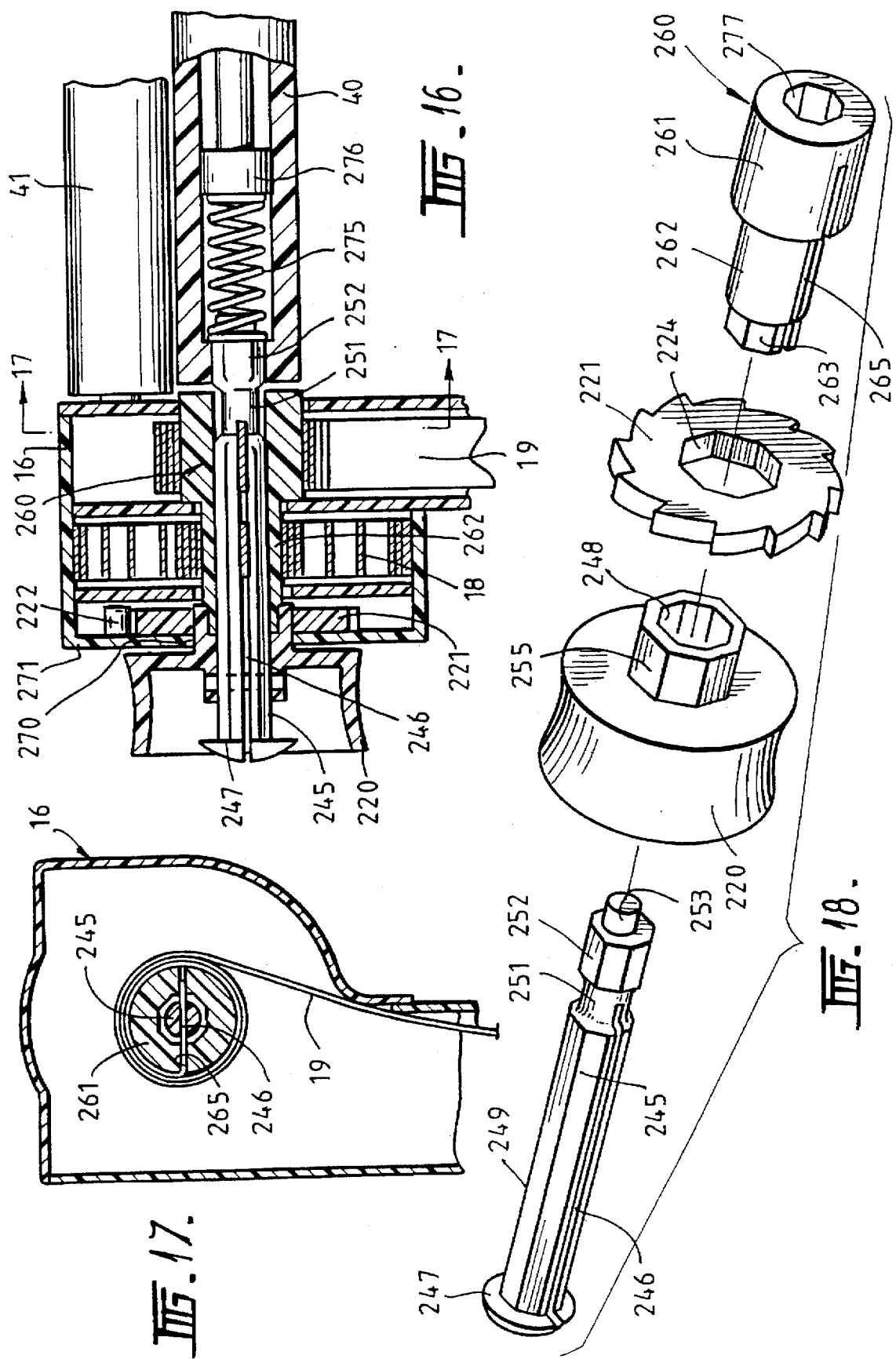

INTRAVENOUS DELIVERY SYSTEM

FIELD OF THE INVENTION

This invention relates to intravenous delivery systems.

BACKGROUND OF THE INVENTION AND SUMMARY OF PRIOR ART

The infusion of large volumes such as 500 to 1000 ml of intravenous solutions is typically carried out by hanging a container above the level of the patient in order to achieve flow by gravity. Infusion can also be achieved by pumps and pressure means and many such devices are known in the art for example, EP 0,321,996 and U.S. Pat. Nos. 4,722,732, 5,735,497 and 5,163,909 all disclose devices of varying complexity that pressurise a solution container to control delivery of intravenous solutions.

The infusion of solution by gravity presents significant problems for staff setting and controlling the infusion rate. With collapsible intravenous solution containers, a further problem encountered is the difficulty in determining the amount of solution infused. The bags are usually transparent with calibrated scales printed on the exterior. The amount of solution delivered is determined by checking where the meniscus of the solution is on the calibrated scale.

Flow rate of solution is typically controlled by adjusting a roller clamp on the plastics tubing which connects the intravenous solution container to the patient. Plastic creep in the tubing at the point of impingement of the roller causes a change in internal dimensions of the tubing and a result change in flow rate. Thus, it is necessary to reset the roller clamp from time to time.

Normal production variations in the wall thickness of the tubing also causes difficulty in setting repeatable flow rates. These problems are further compounded by changes in the head pressure as the intravenous solution container empties. For a one litre bag, the variation in head pressure is in the order of 12%.

A further problem with gravity feed of intravenous solution is that of shutting down flow before the container empties. Because of the changes that occur in flow rates as set forth above, medical staff can expend excessive time in checking the container for runout as it is not possible to assess accurately the time at which a container should empty.

Pressure driven infusion devices exist which correct for all the above difficulties but these devices are expensive and the solution administration sets used with these devices are also expensive. Furthermore, specialist staff is usually required to operate and maintain such pressure driven devices. It is therefore foreseen that there is a need for a cost effective gravity feed intravenous system that is easy to use and reliable. Previous attempts to control pressure variation through change of head pressure in gravity systems have been complicated and expensive and fail to provide a simple and effective means of determining the volume of solution that has been delivered at a particular time. U.S. Pat. Nos. 2,578,374, 2,771,878, 4,137,915 and 4,455,139 disclose examples of such systems.

It is, therefore, an object of the invention to provide an intravenous delivery system that maintains a constant head of pressure.

SUMMARY OF THE INVENTION

According to the present invention there is provided an intravenous delivery system for delivering a volume of solution to a patient intravenously from a solution container positioned above the patient and coupled to the patient via a length of narrow flexible tube, said system comprising frame means to support the solution container above the solution delivery outlet, means to raise the container as it empties to ensure a constant head of pressure, and a pointer displaceable about a calibrated scale on the frame means, the pointer being adapted to move with the container to provide visual indication of the volume of solution delivered to the patient.

Preferably, the solution container is suspended from an arm that extends laterally from the frame means, the pointer being constrained by the frame to move up and down the calibrated scale as the container moves.

In a preferred embodiment, the solution container is a flexible bag that is hung from a roller supported by the frame means, the means to raise the container comprising means to axially rotate the roller to wind the bag onto the roller as it empties. The means to axially rotate the roller is preferably a spring which can be tensioned either by an externally rotatable handle or by downward displacement of the pointer relative to the calibrated scale.

The system preferably also includes an adjustable clamp and cut-off mechanism.

In a preferred embodiment, the periphery of the roller is positioned adjacent an abutment defining a gap which allows the empty portion of the bag to be wound onto the roller but prevents the portion of the bag containing solution from being wound onto the roller whereby the bag is not raised at a rate faster than the release of solution. The abutment is advantageously defined by a second roller supported by the frame means with its axis substantially parallel to the first roller and in close proximity to define the gap therebetween.

According to the present invention there is further provided an intravenous delivery system for delivering a volume of solution to a patient intravenously from a flexible solution bag positioned above the patient and coupled to the patient via a length of narrow flexible tube, said system comprising frame means including a roller adapted to suspend the bag above the solution delivery outlet, means to rotate the roller to wind the bag onto the roller as it empties to ensure a constant head of pressure, a pointer displaceable about a calibrated scale on the frame means, the pointer being coupled to the roller to move with the bag to provide visual indication of the volume of solution delivered to the patient, means to control the rate of flow of solution to the delivery outlet and means to automatically cut-off flow after a predetermined volume of solution has been delivered to the patient.

According to the present invention there is still further provided a flow control and cut-off device adapted to control flow of intravenous fluid through a length of plastics tubing, the device comprising jaws adapted to be in engagement on either side of the tubing, screw threaded adjustment means to effect variation of the spacing of the jaws to vary the flow of fluid within the tube by compressing the wall of the tube, a spring loaded plunger carried by the device and displaceable from a cocked position in which the spring is compressed and the jaws are open to a release position whereby the spring urges the plunger to engage the jaws to close the spacing between the jaws and cut-off flow of fluid in the tube; detent means to hold the plunger in the cocked position; and trigger means coupled to the detent means to release the spring loaded plunger from the cocked position.

DESCRIPTION OF THE DRAWINGS

Embodiments of the present invention will now be described by way of example only with reference to the accompanying drawings in which:

FIG. 1 is a front elevational view of an intravenous delivery system,

FIG. 2 is a side-on elevation view of the system,

FIG. 3 is a cross-sectional view taken along the lines 3—3 of FIG. 1 illustrating an adjustable clamp and cut-off mechanism, FIG. 4 is a cross-sectional view taken along the lines 4—4 of FIG. 3 illustrating an adjustable stop, FIG. 5 is a cross-sectional view taken along the lines 5—5 of FIG. 3 illustrating a cut-off mechanism, FIG. 13 is a cross-sectional view taken along the lines 11—11 of FIG. 12 illustrating operation of the cut-off mechanism, FIG. 14 is a cross-sectional view taken along the lines 12—12 of FIG. 12 illustrating the solution bag wound onto the roller, FIG. 15 is a cross-sectional view similar to FIG. 11 but showing use of a pair of pinch rollers below the roller.

FIG. 16 is a cross-sectional view of one end of the top of a further embodiment of the system, FIG. 17 is a cross-sectional view taken along the lines 15—15 of FIG. 16, FIG. 18 is an exploded perspective view of a shaft, pulley and ratchet shown in FIG. 16.

DESCRIPTION OF PREFERRED EMBODIMENTS

Figure 6:
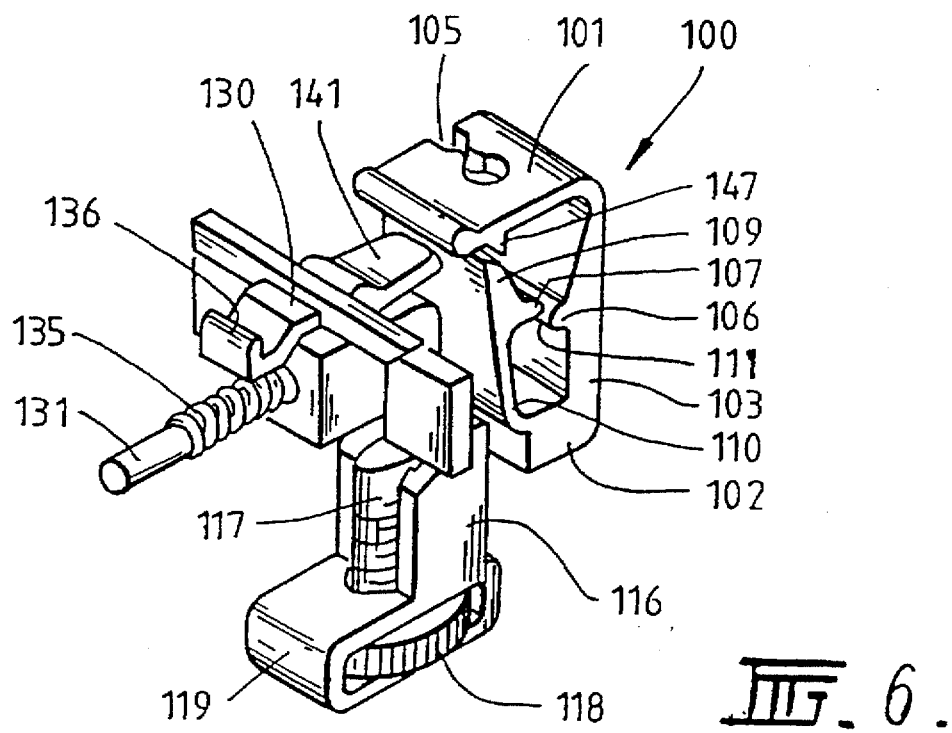
FIG. 6 is a rearward perspective view of the clamp and cut-off mechanism.
Figure 7:
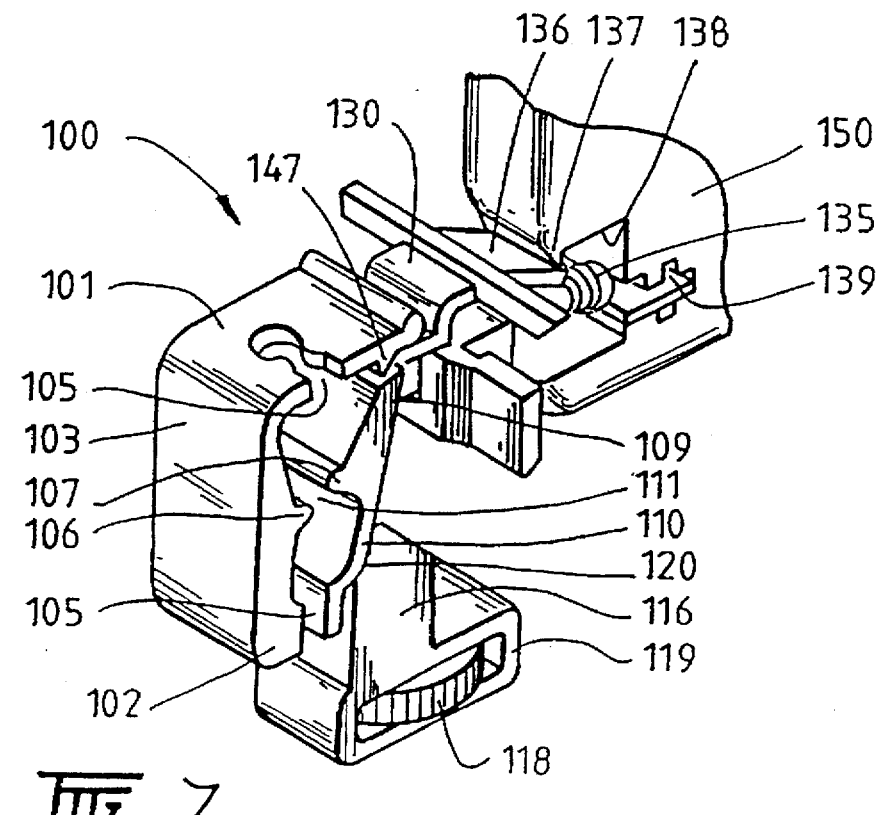
FIG. 7 is a forward perspective view of the clamp and cut-off mechanism.
Figure 8:
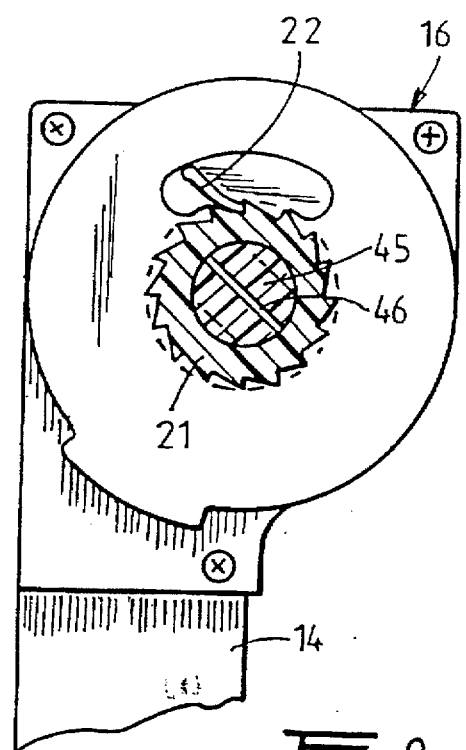
FIG. 8 is a cross-sectional view taken along the lines 6—6 of FIG. 1 illustrating a ratchet and pawl.
Figure 9:
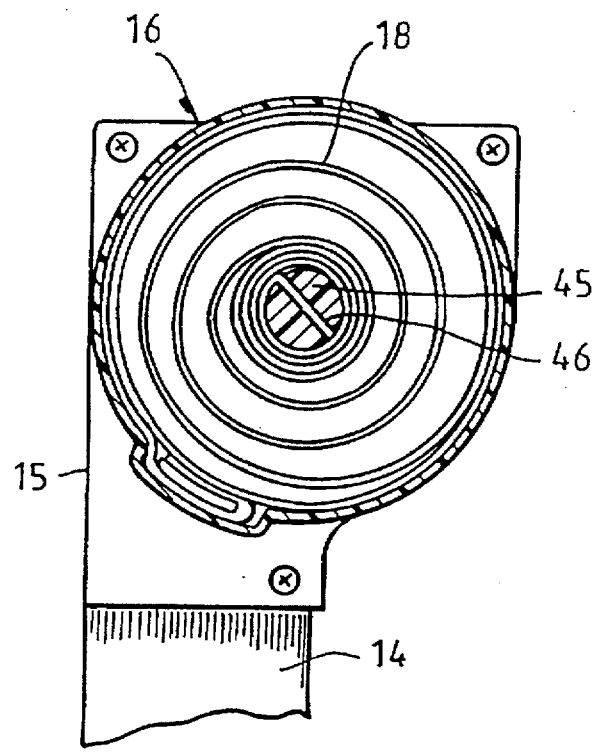
FIG. 9 is a cross-sectional view taken along the line 7—7 of FIG. 1 illustrating the location of a torsion spring in a spool housing.
Figure 10:
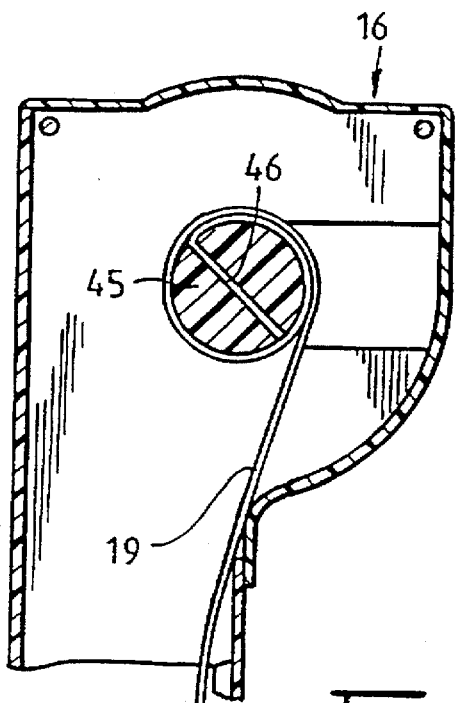
FIG. 10 is a cross-sectional view taken along the lines 8—8 of FIG. 1 illustrating the spool support of a length of tape.

In essence, the intravenous delivery system comprises a frame 10 from which a solution container in the form of a flexible bag 50 is suspended. The system includes a calibrated scale 11 and pointer mechanism 12 that provides clear and positive indication of the amount of fluid that has been expelled from the flexible bag 50. The system also includes means to lift the bag 50 as it empties to ensure a constant head of pressure. The solution is fed by gravity to the patient through a flexible tube 60. In the preferred embodiment, the bag 50 is of flexible transparent plastics and is wrapped around a roller 40 as it empties. However, it is understood that the invention may also embrace a solid solution container that is carried by an overhead arm that is driven to move vertically with respect to the frame as the bag empties. A further feature of the preferred embodiment of the invention is the provision of an adjustable clamp and cut-off mechanism 100 associated with the movable pointer 12 that controls the rate of flow through the flexible tubing 60 and also allows automatic cut off of flow after a predetermined quantity has escaped from the solution bag 50.

As shown in the accompanying drawings particularly with reference to FIG. 1 and 2, the intravenous delivery system comprises an L-shaped frame 10 having a downwardly projecting leg 14 with an outwardly projecting arm 15 having a rear wall 9 and end face 8. The join between the arm and the leg defines a spool housing 16 and the arm 15 is arranged to support a pair of rollers 40 and 41 that are positioned with their longitudinal axes substantially parallel and their peripheries spaced a short distance apart. The rollers 40 and 41 are mounted between the spool housing 16 and end face 8 of the arm 15 to be axially rotatable. The roller 40 is integrally formed at one end with a projecting shaft 45 with an elongate peripheral slit 46. The shaft 45 ends in a flared location button 47. The spool housing 16 supports a spirally wound torsion spring 18 as well as a length of flexible tape 19 both of which have one end located within the slit 46 and are wound onto the shaft 45. The shaft 45 is driven by a handle 20 held by the location button 47. Rotation of the handle is controlled by a ratchet 21 and pawl 22. The elongate leg 14 has an enlarged forwardly facing surface 11 that is furnished with a calibrated scale on either side of a centrally positioned elongate slot 25. The pointer assembly 12 is attached to the end of the flexible tape 19 via a weighted rectangular slide 150 that slides up and down within the channel 27 with the pointer against the calibrated scale 11. The leg 14 is also provided when viewed side on with a similarly calibrated scale 110 as shown in FIG. 2. The component that defines the calibrated scale is in the form of a sleeve 26 that is slidably mounted on the channel 27 of the leg. The position of the sleeve 26 can be adjusted through an adjusting nut and bolt 28 positioned at the base 29 of the sleeve 26.

Figure 11:
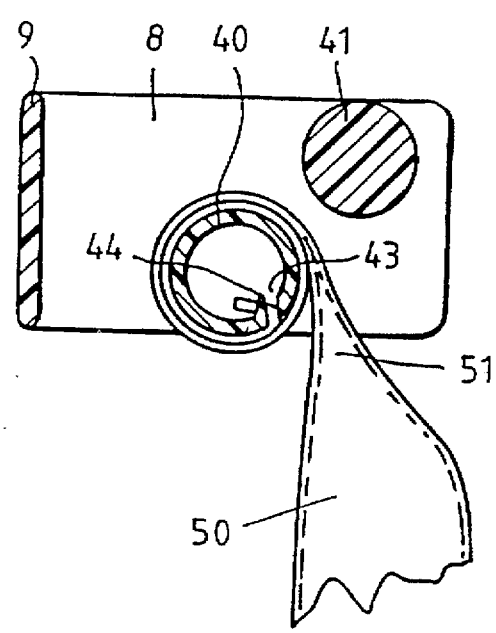
FIG. 11 is a cross-sectional view taken along the lines 9—9 of FIG. 1 illustrating the suspension of a solution bag from a roller.

The frame 10 is adapted to be attached to a post that is usually a free standing post P that would be positioned beside the bed of a patient. Suitable clamping means are used to secure the frame to the post. The laterally projecting arm 15 and rollers 40 and 41 are arranged to support the intravenous solution bag 50 that is made out of transparent flexible plastics. The first roller 40 driven by the handle 20 has formed in its periphery an elongate slot 43 with a centrally positioned hook 44. The end of the flexible bag 50 is provided with a similarly profiled elongate slot (not shown) that extends over the hook 44 (FIG. 11). The bag 50 is hung from the roller 40 as shown in FIG. 1 and is coupled via a drip chamber 55 to the length of thin walled flexible plastics tube 60 which is fed through the adjustable clamp and cut-off device 100 to the patient, not shown. The solution contained in the flexible bag 50 is fed to the patient by gravity. In the illustrated embodiments, the flow of fluid is controlled by the adjustable clamp and cut off mechanism 100 that is attached to the downwardly projecting leg 14 of the frame means 10 via the pointer assembly 12. However, it is understood that the invention in its broadest aspect may embrace a conventional roller clamp control means (not shown) that is simply positioned between the base of the flexible bag 50 and the patient without being directly coupled to the frame 10.

As shown in FIGS. 1 and 2 and in greater detail in FIGS. 8 to 11, the flexible solution bag 50 is lifted as it empties by wrapping the empty end 51 of the bag around the first roller 40. The roller 40 is axially rotated by tensioning the torsion spring 18 that is mounted in the spool housing 16. In the embodiment shown in FIGS. 1 and 2, the handle 20 is mounted externally of the spool housing 16. The handle 20 is rotated to tension the spring 18. The ratchet 21 and pawl 22 prevents rotation of the roller 41 and the bag 50 is suspended from the roller 40 under spring tension. When the system is in use, the pawl 22 on the ratchet 21 is released at which time the spring 18 endeavours to cause the roller 40 to turn to lift the bag. However, the weight of the contents of a full solution bag 50 ensures that there is no rotation of the roller 40 or lifting of the bag until the bag becomes lighter through release of some fluid. As the fluid is released, the spring 18 causes the roller 40 to rotate and the empty end 51 of the bag is wrapped around the roller. The secondary roller 41 is mounted near the periphery of the first roller 40 and ensures that the spring 18 does not overlift the bag 50 especially when nearly empty. As shown in the side on view of FIG. 2, the bag 50 increases in thickness at the top of the meniscus of the liquid. Thus, overlifting of the bag is prevented by the thickened section of the bag caused by the liquid meniscus failing to fit within the gap between the rollers 40 and 41. The handle 20 that tensions the spring 18 is coupled directly to the ratchet 21 but is mounted on the shaft 45 to be axially displaceable. If the handle 20 is pulled back on the shaft 45 to the dotted profile shown in FIG. 1, the ratchet 21 is pulled clear of the pawl 22 which releases the roller 40 and causes the spring 18 to cause the roller to rotate and pull up the bag 50.

Figure 12:
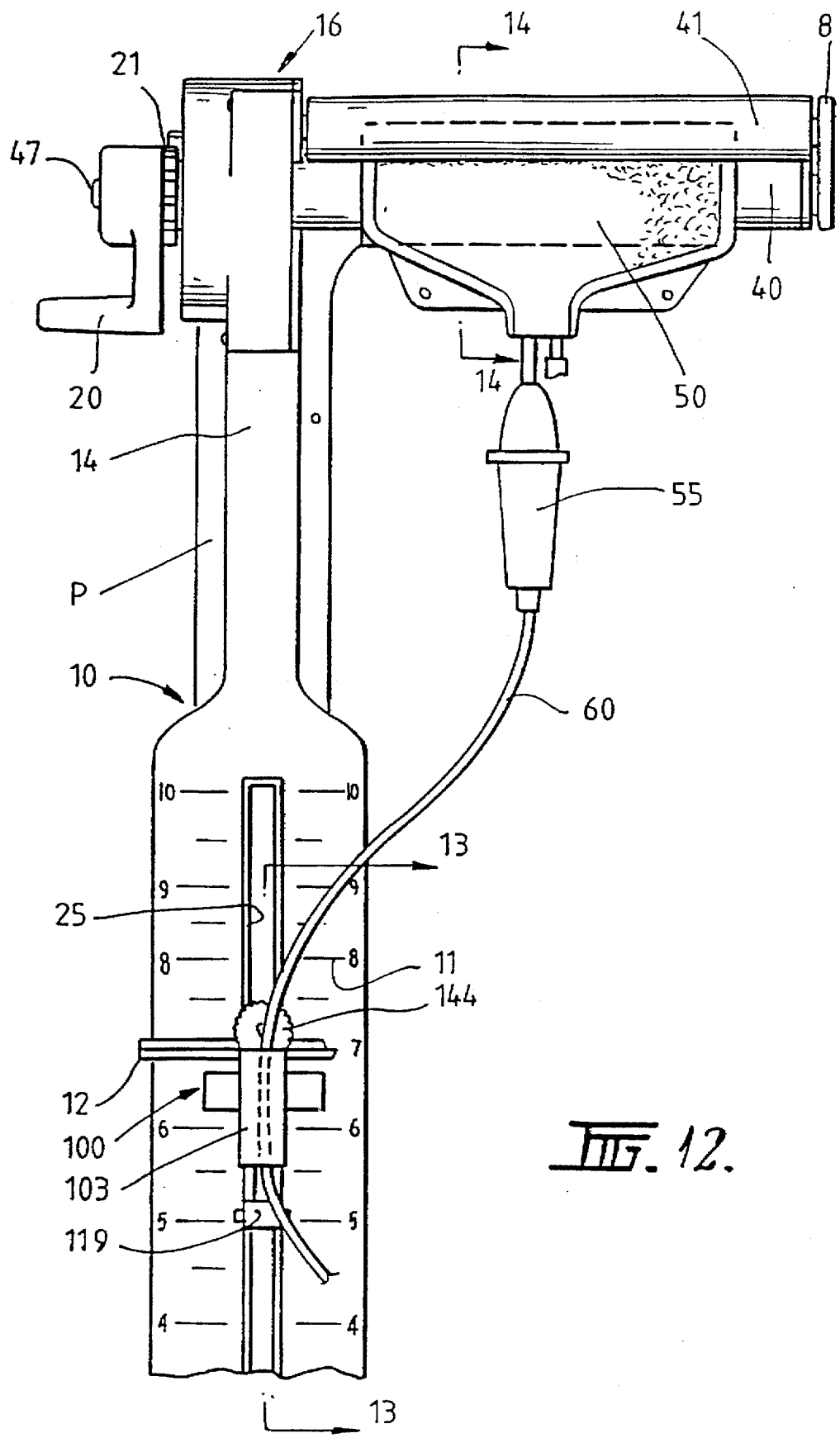
FIG. 12 is a front elevational view of the delivery system when supporting an empty solution bag.

The pointer 12 that moves up and down the calibrated scale 11 is coupled to one end of the flexible tape 19 via the slide 150. With the pointer 12 pulled to its lowest position, it becomes aligned with the zero on the base of the scale meaning that no fluid has been released from the bag 50. As the bag 50 is lifted as it empties by rotation of the roller 40, the shaft 45 in turn rotates, winding up the tape 19 and drawing-up the pointer. As shown in FIG. 12, when the bag 50 is fully empty, the pointer 12 will be adjacent a position on the scale that will indicate an empty bag.

In the embodiment illustrated in FIGS. 16 to 18, the torsion spring 18, instead of being tensioned by rotation of an external handle shown as 20 in the first embodiment, is tensioned by a downward pull on the tape 19 as the pointer 12 is pulled down to the base of the leg to the zero position on the calibrated scale. In this embodiment, the roller 40 is coupled to a separate shaft 245 that has elongate slit 246 and terminates in an enlarged button 247. The handle is replaced by a pulley wheel 220 with a hexagonal internal throughway 248 that accommodates a correspondingly hexagonally profiled exterior 249 of the shaft 245. The opposite end of the shaft includes a smooth waisted portion 251 that merges into another hexagonal portion 252 finally terminating in a cylindrical end projection 253 of reduced cross-section. The pulley 220 is hollow on one side as shown in FIG. 14 to accommodate the end button 247 of the shaft 245. The other side of the roller is provided with a projecting hexagonal spigot 255 on which is mounted a ratchet 221 via a hexagonal centrally positioned aperture 224. A stepped cylindrical sleeve 260 has an enlarged cylindrical end 261 that merges into a smaller cylindrical portion 262 which in turn merges with a hexagonal end portion 263. The sleeve also carries an elongate slit 265 along its periphery. The slit 265 of the sleeve 260 accommodates one end of the torsion spring 18 in the smaller cylindrical portion 263 and one end of the flexible tape 19 in the larger cylindrical portion 261. The larger portion 261 is arranged to be a running fit in the upper portion of the wall of the elongate leg of the device and the hexagonal exterior of the spigot 255 of the pulley 220 is arranged to be a fixed fit within a similar profiled aperture 270 in the end wall 271 of the spool housing 16.

To tension the torsion spring 18, the pointer is pulled down which has the effect of causing the flexible tape 19 to cause the sleeve 260 to rotate. Rotation of the sleeve 260 winds the torsion spring 18 onto the sleeve against its fixed location on the spool housing 16. The ratchet 221 engages a fixed pawl 222 that is formed integrally with the end face of the spool housing 16. In this manner, the spring can be tensioned. The end of the shaft 245 acts against an internally mounted coil spring 275 within the roller 40 against an abutment 276. The coil spring 275 tends to force the shaft 245 outwardly so that the hexagonal end 252 is located within a similarly profiled hexagonal opening 277 on the end face of the pulley 220. In this manner, the pulley 220 rotates with the shaft 245 and the spring 18. To enable the assembly to be loaded with a full solution bag, there is a need to disconnect the roller 40 from the shaft 245. This can be effected by inward pressure on the button 247 thereby compressing the coil spring 275 and moving the hexagonal drive portion 252 clear of the aperture at the end of the roller 40. The stepped cylindrical portion 251 then spins in the aperture allowing the roller 40 to be freely rotatable relative to the shaft 245. In this manner, a bag can be fitted to the roller 40 as in the first embodiment. Once the button 247 is released, the coil spring 275 forces the shaft 245 outwardly to cause re-engagement with the roller 40. The assembly is now ready for operation. To release the tension on the torsion spring 18, it is also possible to pull the pulley 220 rearwardly which has the effect of pulling the spigot 255 and the ratchet 221 that it carries clear of the pawl 222 thereby effecting release of the spring 18. This embodiment has the advantage that there is no need to rotate a handle to tension the device since every time a new bag is fitted to the assembly, the pointer has to be returned to the zero point. The spring can now be tensioned in one operation by simply pulling down the pointer to the zero position on the calibrated scale.

The torsion spring 18 in both embodiments is known to those skilled in the art as a reverse wound reticulated torsion spring. These springs are particularly used for cable rewind mechanisms and in the clock industry and the spring has been calibrated to ensure that it has the desired spring tension to pull up a solution bag as it empties. It is important that the spring is sufficiently strong to lift the bag progressively as it empties to maintain a constant head of pressure. It is understood that those skilled in the art would appreciate that a careful choice of spring has to be made to ensure correct calibration.

In the embodiments shown in the accompanying drawings, the pointer forms part of the adjustable clamping and cut off device 100 through which the flexible delivery tube 60 is passed. Details of this assembly are shown with particular reference to FIGS. 3, 5, 6 and 7. The adjustable clamp and cut off mechanism 100 comprises a plastics moulded component having vertically spaced end walls 101, 102 joined by a vertically extending side wall 103. The end walls 101, 102 each have an elongate slot 105 into which the flexible tube 60 is located. The moulding defines a pair of jaw members 106 and 107. A fixed jaw 106 is formed by projection formed on the inside of the side wall 103. A moveable jaw 107 is formed as an integral extension of the end wall 102. The moveable jaw 107 comprises a head 109 joined by a leaf member 110 that allows the head 109 to resiliently pivot relative to the fixed jaw 106. The two jaws define a narrow gap 111 into which the tube 60 is located as shown in FIG. 3.

The adjustment of the clamp 100 is provided by a forwardly projecting web 115 formed on the base of the clamp assembly to include a vertical pillar 132 which supports a slide 116 that is coupled to a threaded shaft 117 which engages knurled disc 118 carried in a rectangular enclosure 119 that forms part of the slide 116. Rotation of the knurled disc 118 causes the slide 116 to move in a vertical plane up and down the shaft 117. As can be seen in FIG. 3, the tip 120 of the slide 116 engages the base of the leaf 110 of the jaw 107 and movement of the slide 116 upward causes the jaw 107 to move inwardly to adjust the gap 111 between the jaws 106 and 107 and therefore vary the clamping force on the flexible tube 60.

The cut-out mechanism is provided by a spring loaded plunger 130 that is mounted on a horizontal shaft 131 that extends laterally from the pillar 132 formed on the web 115 of the end wall 102 of the plastics moulding. The shaft 131 carries a coil spring 135 and the plunger 130 has a rearwardly extending tail 136 that is arranged to, in a spring loaded manner, clip against a pointed shoulder 137 that is formed on the upper end of a slot 138 formed in the rectangular slide 150 that is secured to the base of the tape 19. The shaft 131 is keyed into a stepped aperture 139 in the rear of the slot 138 so that the weighted slide 150 supports the clamp and cut-off mechanism 100. The plunger 130 includes a forwardly projecting end 141 and, in the loaded and open position, the plunger 130 is depressed as shown in FIG. 3 with the projecting end 141 clear of the rear face of the head 109 of the jaw 107.

An adjustable stop 140 is provided on the front face of the leg of the frame as shown particularly with reference to FIGS. 3 and 4. A plate 142 fits behind the elongate slot 25 in the front of the leg 14 and is coupled to a knurled knob 144 via a threaded shaft 145. This arrangement allows the stop 140 to be adjustably slid up and down the front face of the slot 25 in the leg to a position where cut-off of fluid delivery is required. By positioning the stop 40 and screwing down the knurled knob 144 at, for example the position shown in FIG. 10, the cut off point is determined. As the fluid is delivered from the container, the slide 150 and cut-off mechanism 100 is draw upwardly until the top of the plunger 130 abuts the underside of the stop 140. This causes vertical movement of the plunger 130 to stop and eventually causes the slide 150 to be pulled upwardly so that the downwardly projecting shoulder 137 is clear of the tail 136. Once this is released, the coil spring 135 urges the plunger 130 forwardly so that the projecting end 141 engages the rear of the head 109 of the second jaw 107 forcing the jaw inwardly to compress the tube 60 and cut off flow. This arrangement is shown in FIG. 13. The top wall 101 of the clamp assembly has an over-hanging ledge 146 with a downwardly projecting lip 147 which locates behind the rear of the head 109 of the second jaw 107 holding the jaw in a closed configuration and ensuring against accidental release of the clamping mechanism. The over-hanging ledge 142 and lip 147 provides positive shut-off which can be manually effected to close off the flow when a new bag is being fitted. Once fitted, the cut-off can be released and the stop 40 adjusted prior to operation of the system.

The intravenous fluids delivered by the system would include saline solutions, glucose and blood. It is understood that the system is designed to be useable with all types of intravenous delivery.

In an alternative means of winding up the bag shown in FIG. 15, the upper end 51 of the bag 50 is drawn through a pair of pinch rollers 280 and 281 before being wound onto the spring tension roller 40.

Figure 19:
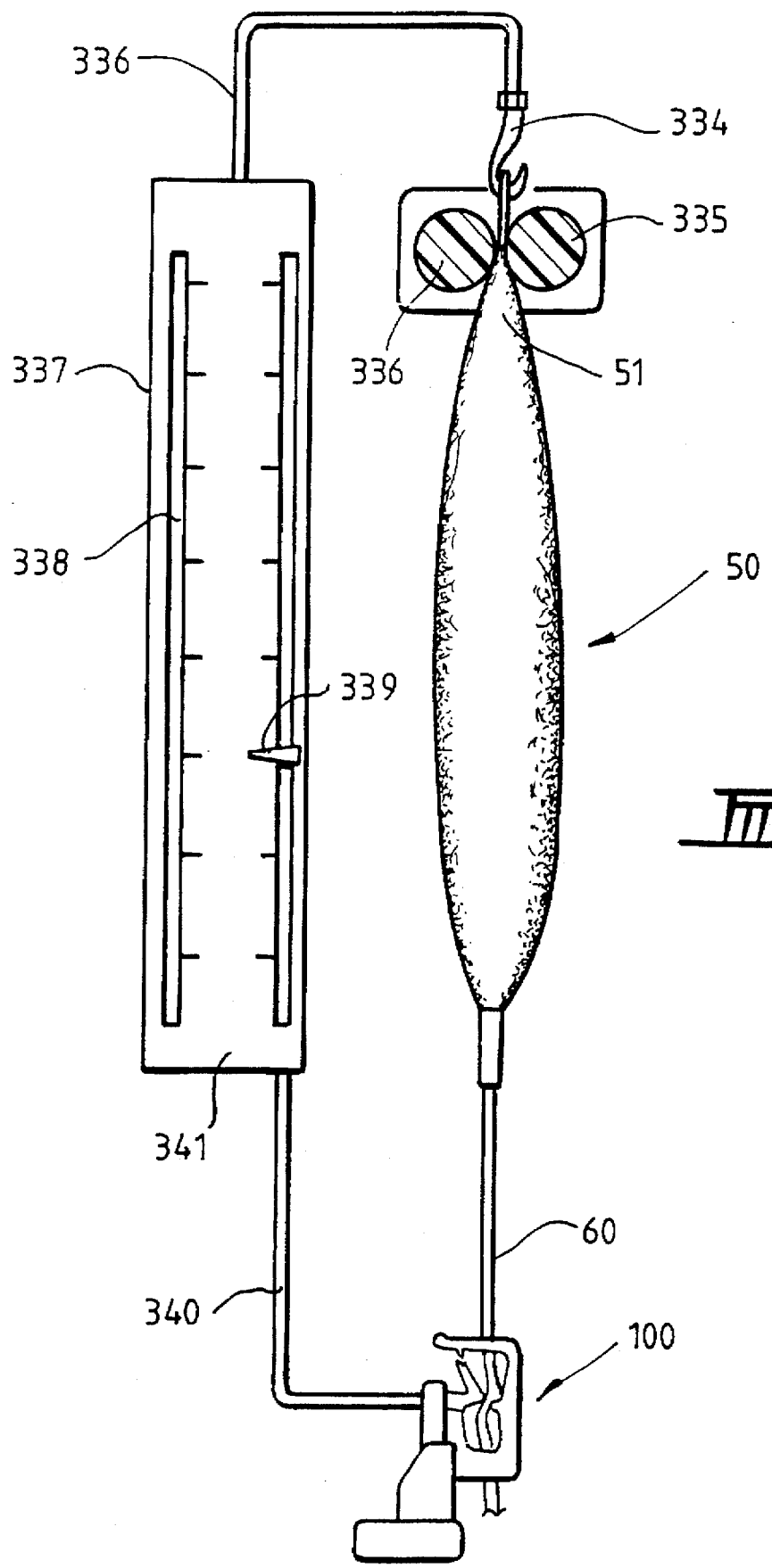
FIG. 19 is a schematic illustration of another embodiment of the invention.

In a still further embodiment illustrated in FIG. 19, the bag 50 is arranged to be pulled between a pair of pinch rollers 335 and 336 similar to those described with reference to the embodiment shown in FIG. 15 by a hanger 334. The rollers 335 and 336 may have a pre-set gap or may be pre-tensioned by a spring or other similar means to squeeze the top end of the bag 51 to apply pressure to the solution as the bag is drawn up through the rollers. The hanger 334 is connected by a drive linkage 336 to an energy accumulator 337. The energy accumulator 337 has a volume infused scale 338 and a required volume set scale 339 provided on a front face 341. There is a further linkage 340 from the energy accumulator 337 to a flow adjustment and cut-off device 100 of the kind similar to that described in the earlier embodiments. The adjustable flow and cut-off device is illustrated schematically in FIG. 19. The energy accumulator 337 may be in any convenient form such as a gas strut, a compression or tension spring, counter balance weight, hydraulic or pneumatic cylinders or electrically driven servo-motor or clock work mechanism. The drive linkage 336 may be a cable that passes around a pulley, a solid rod or pneumatic, hydraulic or electro-mechanical linkage. The device may be mounted on a pole (not shown) similar to the pole shown in the earlier embodiments.

Whilst in the preferred embodiments the solution container is a flexible plastics bag, it is understood that this system could be modified to accommodate a rigid solution container. In this case, the system would be adapted so that the container is clamped to a pole and moves up and down the pole as the rigid container empties.

Further features of the device that are not illustrated in the accompanying drawings concern the provision of visual or audio alarms that provide warning signals when the container is almost empty.

A further use of the system described above could be modified to provide a pressure infusion device that operates independently of gravity. A device of this kind would be especially used in emergency situations such as with ambulances and as a portable unit that can be used in certain home therapy situations. When used in this situation, the pinch rollers would be used to apply pressure to the fluid within the bag to force the fluid out of the bag and into the patient via the flow control mechanisms.

The intravenous delivery system described above has been designed to be a simple and effective means of operating gravity fed intravenous delivery. The device provides a ready indication of the volume of solution delivered and provides easy to operate means of adjusting the rate of flow including a mechanism for adjusting the cut-off to terminate flow of solution. The device has the additional advantage that through lifting the bag as it empties, a constant head of pressure is maintained. It is envisaged that devices of the kind described above can be mass produced at reasonable prices so that hospitals and other medical centres can ensure that each patient bed has access to a system. The device is simple to use and does not require constant adjustment. It has also been designed to ensure ease of reading so that the nursing staff can monitor the delivery of solution by casual inspection from a distance. Whilst being easy to operate and competitively priced, it is envisaged that the system would be both reliable in the senses of durability and accuracy.

We claim:

1. An intravenous delivery system containing a solution delivery outlet for delivering a volume of solution to a patient intravenously from a solution container positioned above the patient and coupled to the patient via a length of narrow flexible tube, said system comprising frame means to support the solution container above the solution delivery outlet, means to raise the container as it empties to ensure a constant head of pressure, pointer displaceable about a calibrated scale on the frame means, the pointer being adapted to move with the container to provide visual indication of the volume of solution deliver to the patient, cut-off means to prevent flow of solution through the tube and means to trigger the cut-off means in response to a preselected position of the pointer.

2. The intravenous delivery system according to claim 1 wherein the solution container is suspended from an arm that extends laterally from the frame means, the pointer being constrained by the frame to move up and down the calibrated scale as the container moves.

3. The intravenous delivery system according to claim 1 wherein the solution container is a flexible bag that is hung from a roller supported by the frame means, the means to raise the container comprising means to axially rotate the roller to wind the bag onto the roller as it empties.

4. The intravenous delivery system according to claim 3 wherein the pointer is coupled to the roller whereby rotation of the roller in one direction pulls the pointer up the calibrated scale.

5. The intravenous delivery system according to claim 4 wherein the means to axially rotate the roller comprises spring means mounted on the frame means and capable of being tensioned to cause the roller to rotate.

6. The intravenous delivery system according to claim 5 wherein the means to tension the spring means comprises a handle that acts to rotate the roller against the spring means, and a ratchet and pawl to control return of the roller against the spring means.

7. The intravenous delivery system according to claim 5 wherein the means to tension the spring means comprises the pointer that is coupled to the roller to tension the spring as the pointer is pulled down to zero the calibration.

8. The intravenous delivery system according to claim 5 wherein the spring means comprises a torsion spring, the spring force of which is selected to ensure rotation of the roller as the solution bag empties.

9. The intravenous delivery system according to claims 3 wherein the roller is provided with an elongated slot including a centrally positioned location peg from which the flexible bag may be hung.

10. The intravenous delivery system according to claim 3 wherein the periphery of the roller is positioned adjacent an abutment defining a gap which allows the empty portion of the bag to be wound onto the roller but prevents the portion of the bag containing solution from being wound onto the roller whereby the bag is not raised at a rate faster than the release of solution.

11. The intravenous delivery system according to claim 10 wherein the abutment comprises a second roller supported by the frame means with its axis substantially parallel to the first roller and in close proximity to define the gap therebetween.

12. The intravenous delivery system according to claim wherein the delivery outlet includes an adjustable clamp to control flow of solution.

13. The intravenous delivery system according to claim 1 wherein the means to cut off flow is a spring loaded plunger which when released causes the clamp to close off flow in the tube.

14. The intravenous delivery system according to claim 13 wherein the means to cut off the flow is controlled by a moveable stop which when engaged by the pointer releases the spring loaded plunger.

15. The intravenous delivery system according to claim 14 wherein the position of the stop is adjustable along the calibrated scale so that flow can be cut off at a selected position corresponding to selected volume discharge.

16. The intravenous delivery system according to claim 8 wherein the means to clamp the solution outlet comprises a pair of jaws positioned on either side of the flexible tube and the means to cut-off flow comprises a spring loaded plunger displaceable from an inoperative position when the jaws are open to an operative position whereby the plunger forces the jaws to compress the tube to close off flow.

17. The intravenous delivery system according to claim 16 wherein a screw threaded adjustment means is provided to adjust the spacing of the jaws.

* * * * *